United States Patent
Chastaing et al.

(12)

(10) Patent No.: US 6,264,935 B1
(45) Date of Patent: Jul. 24, 2001

(54) OPHTHALMIC COMPOSITION CONTAINING A CARBONIC ANHYDRASE INHIBITOR AND XANTHAN GUM

(75) Inventors: Gilles Chastaing, Beaumont; Bernard Plazonnet, Clermont-Ferrand; Annouk Rozier, Riom, all of (FR)

(73) Assignee: Laboratoires MSD - Chibret, Paris (FR)

( * ) Notice: Subject to any disclaimer, the term of this patent is extended or adjusted under 35 U.S.C. 154(b) by 0 days.

(21) Appl. No.: 09/284,718

(22) PCT Filed: Oct. 9, 1997

(86) PCT No.: PCT/EP97/05678

§ 371 Date: Jun. 14, 1999

§ 102(e) Date: Jun. 14, 1999

(87) PCT Pub. No.: WO98/17249

PCT Pub. Date: Apr. 30, 1998

(30) Foreign Application Priority Data

Oct. 17, 1996 (FR) .................................... 96 12658

(51) Int. Cl.⁷ .............................. A61K 31/74; A61F 2/14
(52) U.S. Cl. ...................... 424/78.04; 424/427; 424/428; 514/782; 514/913
(58) Field of Search ................. 424/78.04, 427, 424/428; 514/782, 913

(56) References Cited

U.S. PATENT DOCUMENTS

| 4,136,173 | 1/1979 | Pramoda et al. . |
| 4,136,177 | 1/1979 | Lin et al. . |
| 4,136,178 | 1/1979 | Lin et al. . |
| 5,318,780 | * 6/1994 | Viegas et al. ........................ 424/427 |

FOREIGN PATENT DOCUMENTS

| 0 227 494 A1 | 7/1987 | (EP) . |
| 0 227 494 B1 | 7/1987 | (EP) . |
| 0 296 879 A1 | 12/1988 | (EP) . |
| 0 296 879 B1 | 12/1988 | (EP) . |
| 0 375 320 | 6/1990 | (EP) . |
| 0 382 537 | 8/1990 | (EP) . |
| 0 411 704 A1 | 2/1991 | (EP) . |
| 0 437 368 A1 | 7/1991 | (EP) . |
| 0 452 151 A1 | 10/1991 | (EP) . |
| 0 455 396 A1 | 11/1991 | (EP) . |
| 0 457 586 A1 | 11/1991 | (EP) . |
| 0 479 480 A21 | 4/1992 | (EP) . |
| 0 495 421 A1 | 7/1992 | (EP) . |
| 0 507 224 A2 | 10/1992 | (EP) . |
| WO 91/14430 | 10/1991 | (WO) . |
| WO 9114682 | 10/1991 | (WO) . |
| WO 9114683 | 10/1991 | (WO) . |
| WO 92/00287 | 1/1992 | (WO) . |
| WO 94/06411 | 3/1994 | (WO) . |
| WO 94/27578 | 12/1994 | (WO) . |
| WO2000004899A | 2/2000 | (WO) . |

OTHER PUBLICATIONS

J. Grove & B Plazonnet, *S.T.P. Pharma Sciences* 2(1) p 76–80 (1992).

* cited by examiner

*Primary Examiner*—Carlos A. Azpuru
(74) *Attorney, Agent, or Firm*—Sylvia A. Ayler; Mark R. Daniel

(57) ABSTRACT

The present invention relates to ophthalmic compositions for the treatment of ocular hypertension and glaucoma, comprising a hypotonic solution of 0.1 to 0.2% (w/w) of xanthan gum and 0.5 to 5% (w/w) of a topical carbonic anhydrase inhibitor or an ophthalmologically acceptable salt thereof.

13 Claims, No Drawings

OPHTHALMIC COMPOSITION CONTAINING A CARBONIC ANHYDRASE INHIBITOR AND XANTHAN GUM

This application is a 371 PCT/EP97/05678 filed Oct. 9, 1997, which claims priority from FR96/12658, filed Oct. 17, 1996.

SUMMARY OF THE INVENTION

This invention relates to novel ophthalmic compositions comprising a hypotonic solution of xanthan gum and a topical carbonic anhydrase inhibitor.

The invention is also concerned with the use of the novel ophthalmic compositions in the treatment of ocular hypertension and glaucoma..

More particularly, it relates to such ophthalmic compositions and their use in the treatment of ocular hypertension and glaucoma, wherein the topical carbonic anhydrase inhibitor is (S,S)-(−)-5,6-dihydro-4-ethylamino-6-methyl-4H-thieno[2,3-b]thiopyran-2-sulphonamide-7,7-dioxide, or an ophthalmologically acceptable salt thereof.

BACKGROUND OF THE INVENTION

Glaucoma is a degenerative disease of the eye wherein the intraocular pressure is too high to permit normal eye function. As a result, damage may occur to the optic nerve head and result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by the majority of ophthalmologists to represent merely the earliest phase in the onset of glaucoma.

Many of the drugs formerly used to treat glaucoma proved to be not entirely satisfactory. The early methods of treatment of glaucoma employing pilocarpine produced undesirable local effects that made this drug, though valuable, unsatisfactory as a first line drug. More recently, clinicians have noted that many β-adrenergic antagonists are effective in reducing intraocular pressure. While many of these agents are effective for this purpose, there exist some patients with whom this treatment is not effective or not sufficiently effective. Many of these agents also have other characteristics, e.g., membrane stabilising activity, that become more apparent with increased doses and render them unacceptable for chronic ocular use.

The β-adrenergic antagonist, timolol, was found to reduce intraocular pressure and to be devoid of many unwanted side effects associated with pilocarpine and, in addition, to possess advantages over many other β-adrenergic antagonists, e.g., to be devoid of local anaesthetic properties, to have a long duration of activity, and to display minimal loss of effect with increased duration of dosing.

Although pilocarpine and β-adrenergic antagonists reduce intraocular pressure, none of these drugs manifests its action by inhibiting the enzyme carbonic anhydrase, and thus they do not take advantage of reducing the contribution to aqueous humor formation made by the carbonic anhydrase pathway.

Agents referred to as carbonic anhydrase inhibitors block or impede this inflow pathway by inhibiting the enzyme carbonic anhydrase. While such carbonic anhydrase inhibitors are now used to treat intraocular pressure by systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective.

For several years, the desirability of directing the carbonic anhydrase inhibitor to only the desired ocular target tissue has been recognised. Because carbonic anhydrase inhibitors have a profound effect in altering basic physiological processes, the avoidance of a systemic route of administration serves to diminish, if not entirely eliminate, those side effects caused by inhibition of carbonic anhydrase such as metabolic acidosis, vomiting, numbness, tingling, general malaise and the like.

Recently, a topically effective carbonic anhydrase inhibitor has become available for clinical use. (S,S)-(−)-5,6-Dihydro-4-ethylamino-6-methyl-4H-thieno[2,3-b]thiopyran-2-sulfonamide-7,7-dioxide hydrochloride (dorzolamide HCl; MK507) is the active ingredient in TRUSOPT™ which is prescribed for the treatment of elevated intraocular pressure in ocular hypertension, open-angle glaucoma and pseudo-exfoliative glaucoma. TRUSOPT™ Ophthalmic Solution is applied as an isotonic, buffered, slightly viscous, aqueous solution of dorzolamide HCl. Each ml of TRUSOPT™ 2% contains 20 mg dorzolamide (22.3 mg dorzolamide HCl). When used as monotherapy, the dose is one drop of TRUSOPT™ Ophthalmic Solution in the conjunctival sac of each affected eye three times daily.

The activity of dorzolamide HCl and of other topical carbonic anhydrase inhibitors currently under development wanes 6 to 8 hours post-dose, meaning that as single agents these carbonic anhydrase inhibitors must be administered at least three times a day to maintain the desired lowering of intraocular pressure. The composition of the present invention maintains the desired lowering of intraocular pressure for a full twelve hours. Because of this increased duration of action, the composition disclosed herein is effective when administered only twice a day. Patient compliance is anticipated to be greater with twice a day administration than with three times a day administration.

Grove et al, *S.T.P. Pharma Sciences*, 2(1), 76–80 (1992) describe the effects of hypotonicity upon a hydroxyethyl cellulose (HEC) solution of the topical carbonic anhydrase inhibitor, 5-(3-dimethylaminoethyl-4-hydroxyphenylsulfonyl)thiophene-2-sulfonamide hydrochloride.

International (PCI) Publication No. WO 94/27578 describes drug delivery compositions comprising a liquid hypotonic solution of at least one hydrophilic polymer of the type which undergoes liquid-gel phase transition gelling in situ in contact with a physiological solution, and a pharmaceutically active compound.

U.S. Pat. No. 4,136,173 (Pramoda et al) published Jan. 23, 1979 describes ophthalmic compositions containing xanthan gum and locust bean gum which are pH sensitive and which gel upon instillation.

U.S. Pat. No. 4,136,177 (Lin et al) published Jan. 23, 1979 describes ophthalmic compositions comprising an ophthalmic drug and xanthan gum.

U.S. Pat. No. 4,136,178 (Lin et al) published Jan. 23, 1979 describes ophthalmic compositions comprising an ophthalmic agent and locust bean gum.

European Patent Specification No. 0 507 224-A describes combinations of gelling polysaccharides and finely divided drug carrier substrates in topical ophthalmic compositions which are adminstrable as a drop and which gel upon instillation.

U.S. Pat. No. 5,318,780 (Viegas et al) published Jun. 7, 1994 also relates to uses of in situ formed gels, in which compositions are prepared combining a film-forming water soluble polymer and an ionic polysaccharide, and optionally a latent counter-ion to gel the polysaccharide upon release of the counter ion.

DETAILED DESCRIPTION OF THE INVENTION

The novel ophthalmic compositions of this invention comprise a hypotonic solution of xanthan gum and a therapeutically effective amount of a topical carbonic anhydrase inhibitor.

Following administration of a composition of the present invention to the conjunctival sac of a patient's eye, there is no liquid-gel phase transition. The advantageous enhancement in ocular bioavailability of the topical carbonic anhydrase inhibitor is achieved through the unique combination of the properties of the hypotonic solution of xanthan gum.

Xanthan gum is a high molecular weight polysaccharide gum obtainable from the aerobic fermentation of a carbohydrate with bacteria of the genus Xanthomonas, especially *Xanthomonas campestris*. Each xanthan gum repeat unit contains five sugar residues: two glucose, two mannose and one glucuronic acid. The polymer backbone consists of four β-D-glucose units linked at the 1 and 4 positions. Trisaccharide side chains on alternating anhydroglucose units distinguish xanthan gum from cellulose. Each side chain comprises a glucuronic acid residue between two mannose units. At most of the terminal mannose units is a pyruvate moiety.

Xanthan gum solutions are pseudoplastic. In other words, when shear stress is increased, the viscosity is progressively reduced. Upon reduction of the shear, total viscosity is recovered almost instantaneously. This behaviour results from the high-molecular-weight molecule which forms complex molecular aggregates through hydrogen bonds and polymer entanglement. Also, this highly ordered network of entangled, stiff molecules accounts for the high viscosity observed at low shear rates. Shear thinning results from disaggregation of this network and alignment of individual polymer molecules in the direction of shear force. However, when the shearing ceases, aggregates re-form rapidly. As a result of its helical conformation, xanthan gum viscosity is relatively insensitive to temperature changes below the transition temperatures and to differences in ionic strength and pH. Xanthan gum solutions do not therefore have any liquid-gel phase transition properties, hence xanthan gum is not suitable for use in the formulation of in situ gelling solutions.

The results of the formulations of the present invention suggest that the high degree of pseudoplasticity, which is independent of concentration, appears to be important in contributing to the unusual ocular penetration properties of the hypotonic formulation of xanthan gum.

Therapeutic composition containing xanthan gum and locust bean gum which are delivered in liquid form and which gel upon instillation have been reported (see U.S. Pat. No. 4,136,173). Xanthan gum alone is a viscosifying agent but not a gelling agent. The present invention expressly excludes co-formulation with other polymers such as locust bean gum.

Other in situ gel forming compositions which additionally contain an ionic polysaccharide and optionally a latent counter-ion to gel the polysaccharide upon release of the counter-ion have also been reported (see U.S. Pat. No. 5,318,780). The present invention expressly excludes co-formulation with ionic polysaccharides, with or without latent counter-ions.

Xanthan gum is commercially available, for example, under the tradename KELTROL™ from Monsanto Performance Materials, a unit of Monsanto Company, St. Louis, Mo. 63167, USA.

In the novel compositions of the present invention, the concentration of xanthan gum comprises about 0.1 to 2% (w/w), preferably 0.4 to 0.7% (w/w). Particularly preferred is KELTROL™ xanthan gum from Monsanto Performance Materials.

The topical carbonic anhydrase inhibitors of use in the novel compositions of the present invention include those compounds described in European Patent Specification Nos. 0 296 879, 0 375 320, 0 382 537, 0 411 704, 0 452 151, 0 457 586 and 0 479 480; and International (PCT) Publication Nos. WO 91/14430, WO 91114682, WO 91/14683, WO 92/00287 and WO 94/06411.

Particularly preferred topical carbonic anhydrase inhibitors for use in the novel compositions of the present invention is the class of compounds of the structural formula (I):

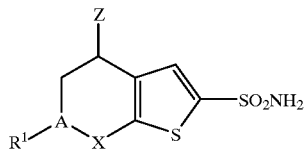

(I)

an individual diastereomer, an individual enantiomer or mixture thereof, or an opthalmologically acceptable salt thereof, wherein:

A is carbon or nitrogen, preferably carbon;

Z is —NHR or —OR, preferably —NHR;

R is $C_{1-6}$alkyl, either straight or branched chain, preferably $C_{2-4}$alkyl such as ethyl, propyl or isobutyl;

$R^1$ is
  (a) hydrogen,
  (b) $C_{1-3}$alkyl, Preferably methyl, ethyl or n-propyl, or
  (c) $C_{1-4}$alkoxy-$C_{1-4}$alkyl, preferably 3-methoxypropyl or ethoxymethyl; and X is —S(O)$_2$— or —C(O)—, preferably —S(O)$_2$—.

The carbon atoms to which Z and $R^1$ are bonded may be chiral. When named according to absolute configuration, e.g., (R,S) or (S,S), the first letter represents the chirality the carbon atom to which Z is bonded and the second letter represents the chirality of A when A is carbon. The carbonic anhydrase inhibitors of this invention accordingly may be used as diastereomeric mixtures or single enantiomers or as racemic mixtures.

Preferred topical carbonic anhydrase inhibitors for use in the novel compositions of the present invention are compounds of formula (I), above, wherein A is carbon; and wherein R is —CH$_2$CH$_3$ and $R^1$ is —CH$_3$; or R is —CH$_2$CH$_2$CH$_3$ and $R^1$ is —CH$_2$CH$_2$CH$_2$OCH$_3$; or R is —CH$_2$CH$_3$ and $R^1$ is —CH$_2$CH$_2$CH$_3$; or $R^1$ is —CH$_2$CH$_2$(CH$_3$)$_2$ and $R^1$ is hydrogen; or $R^1$ is —CH$_2$CH$_3$ and $R^1$ is —CH$_2$OCH$_2$CH$_3$; and carbons 4 and 6 of the topical carbonic anhydrase inhibitor both have S absolute stereochemical configuration.

A particularly preferred topical carbonic anhydrase inhibitor for use in the novel compositions of the present invention is dorzolamide, especially as its hydrochloride salt.

The novel ophthalmic formulations of this invention comprise about 0.05 to 5% (w/w) of the topical carbonic anhydrase inhibitor, usually about 0.5 to 3% (w/w), to be administered once or twice daily, to each affected eye.

The novel method of this invention comprises the topical ocular administration of about 0.025 to 5 mg per day, preferably about 0.25 to 3 mg per day, of the topical carbonic anhydrase inhibitor to each eye.

As a unit dosage, between 0.025 and 2.5 mg, preferably between 0.25 and 1.5 mg, of the topical carbonic anhydrase inhibitor is applied to each eye.

Conventional ophthalmic solutions are usually prepared as isotonic solutions using tonicity adjusting agents such as potassium chloride, sodium chloride, mannitol, dextrose and glycerin. An isotonic solution will have a freezing point depression of approximately −0.54° C. Tonicity may also be measured by the osmolality of the solution, an isotonic solution having an osmolality of about 290 milliosmoles per kilogram (mOs/kg).

It is a characteristic of the ophthalmic compositions of the present invention that they are hypotonic solutions, with a freezing point depression between about −0.28° C. and −0.4° C., and preferably between about −0.31° C. and −0.37° C.

Alternatively, the hypotonicity of the ophthalmic solutions of the present invention is between about 150 and 215 mOs/kg, and preferably between 170 and 200 mOs/kg.

According to a further aspect of the present invention, there is provided novel ophthalmic compositions comprising a hypotonic solution of xanthan gum, a therapeutically effective amount of a topical carbonic anhydrase inhibitor and a therapeutically effective amount of a β-adrenergic receptor blocking agent. Suitable β-adrenergic receptor blocking agents include betaxolol, bufetolol, carteolol, levobunolol, metipranolol, and timolol, or an ophthalmologically acceptable salt thereof. A particularly preferred β-adrenergic receptor blocking agent is timolol maleate.

Such compositions preferably comprise about 0.05 to 5% (w/w) of the topical carbonic anhydrase inhibitor, usually about 0.5 to 3% (w/w), and about 0.01 to 1% (w/w) of the β-adrenergic receptor blocking agent, preferably about 0.1 to 0.5% (w/w) to be administered once or twice a day to each affected eye.

Thus, a further novel method of this invention comprises the topical ocular administration of about 0.025 to 5 mg per day, preferably about 0.25 to 3 mg per day, of the topical carbonic anhydrase inhibitor and about 0.005 to 1 mg per day, preferably about 0.05 to 0.5 mg per day, of the β-adrenergic receptor blocking agent to each eye.

As a unit dosage, between 0.005 and 0.5 mg of the β-adrenergic receptor blocking agent, and preferably between 0.05 and 0.25 mg of the β-adrenergic receptor blocking agent, is applied to each eye.

Suitable subjects for the administration of the formulation of the present invention include primates, man and other animals, particularly man and domesticated animals such as cats and dogs.

The pharmaceutical preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

The following examples of ophthalmic formulations are given by way of illustration.

EXAMPLE 1

| SOLUTION COMPOSITION | | A | B |
|---|---|---|---|
| (S,S)-(-)-5,6-Dihydro-4-ethylamino-6-methyl-4H-thieno[2,3-b]thiopyran-2-sulfonamide-7,7-dioxide monohydrochloride | | 2.226% | 2.226% |
| Xanthan Gum | | 0.5% | 0.7% |
| Sodium Chloride | | 0.2% | 0.2% |
| Benzalkonium Chloride | | 0.0075% | 0.0075% |
| Sodium hydroxide | QS | pH 5.65 | pH 5.65 |
| Purified Water | QS | 100% | 100% |

The active compound, sodium chloride and benzalkonium chloride were dissolved in purified water. The pH of the composition was adjusted to 5.65 by addition of 0.2 N sodium hydroxide solution, and purified water was added until the weight of composition was equal to 75 parts of the final weight (Example 1A) or 65 parts of the final weight (Example 1B). The composition was sterilised by filtration, and the solution flushed with sterile nitrogen. Then a clarified, steam sterilised concentrate of 2% xanthan gum was added to the solution of drug and the obtained solution was homogenised by stirring. The solution was aseptically subdivided into sterile vials and sealed.

EXAMPLE 2

SOLUTION COMPOSITION

| (S,S)-(-)-5,6-Dihydro-4-ethylamino-6-(n-propyl)-4H-thieno[2,3-b]thiopyran-2-sulfonamide-7,7-dioxide monohydrochloride | | 0.88% |
|---|---|---|
| Xanthan Gum | | 0.5% |
| Sodium Citrate | | 0.147% |
| Hydrochloric Acid | QS | pH 5.0 |
| Sorbitol | | 1.5% |
| Benzalkonium Chloride | | 0.0075% |
| Purified Water | QS | 100% |

The active compound, sodium citrate, benzalkonium chloride and sorbitol are dissolved in purified water. The pH of the composition is adjusted to pH 5.0 by addition of hydrochloric acid, and purified water is added until the weight of the composition is equal to 75 parts of the final weight. The composition is sterilised by filtration, flushing with sterile nitrogen. Then a clarified, steam sterilised concentrate of 2% xanthan gum is added to the solution of the drug and the obtained solution is homogenised by stirring. The solution is aseptically subdivided into sterile vials and sealed.

EXAMPLE 3

SOLUTION COMPOSITION

| (±)-5,6-dihydro-4-[(2-methylpropyl)amino]-4H-thieno[2,3-b]thiopyran-2-sulfonamide-7,7-dioxide monohydrochloride | | 1.662% |
|---|---|---|
| Xanthan Gum | | 0.5% |
| Sodium Citrate | | 0.22% |
| Sodium Hydroxide | QS | pH 5.6 |

EXAMPLE 3

SOLUTION COMPOSITION

| | | |
|---|---|---|
| Mannitol | | 0.50% |
| Benzalkonium Chloride | | 0.0075% |
| Purified Water | QS | 100% |

The active compound, sodium citrate, benzalkonium chloride and mannitol are dissolved in purified water. The pH of the composition is adjusted to pH 5.6 by addition of sodium hydroxide, and purified water is added until the weight of the composition was equal to 75 parts of the final weight. The composition is sterilised by filtration, flushing with sterile nitrogen. Then a clarified, steam sterilised concentrate of 2% xanthan gum is added to the solution of the drug and the obtained solution is homogenised by stirring. The solution is aseptically subdivided into sterile vials and sealed.

EXAMPLE 4

SOLUTION COMPOSITION

| | | |
|---|---|---|
| (S,S)-(-)-5,6-dihydro-4-ethylamino-6-methyl-4H-thieno[2,3-b]thiopyran-2-sulfonamide-7,7-dioxide monohydrochloride | | 1.6695% |
| Xanthan Gum | | 0.7% |
| Sodium Chloride | | 0.25% |
| Sodium Hydroxide | QS | pH 5.8 |
| Benzalkonium Chloride | | 0.0075% |
| Purified Water | QS | 100% |

The active compound, sodium chloride and benzalkonium chloride were dissolved in purified water. The pH of the composition was adjusted to pH 5.8 by addition of sodium hydroxide, and purified water was added until the weight of the composition was equal to 65 parts of the final weight. The composition was sterilised by filtration, flushing with sterile nitrogen. Then a clarified, steam sterilised concentrate of 2% xanthan gum was added to the solution of the drug and the obtained solution was homogenised by stirring. The solution was aseptically subdivided into sterile vials and sealed.

EXAMPLE 5

SOLUTION COMPOSITION

| | | |
|---|---|---|
| (S,S)-(-)-5,6-dihydro-4-ethylamino-6-methyl-4H-thieno[2,3-b]thiopyran-2-sulfonamide-7,7-dioxide monohydrochloride | | 1.113% |
| Xanthan Gum | | 0.7% |
| Sodium Hydroxide | QS | pH 6.0 |
| Sodium Chloride | | 0.32% |
| Benzalkonium Chloride | | 0.0075% |
| Purified Water | QS | 100% |

The active compound, sodium chloride and benzalkonium chloride were dissolved in purified water. The pH of the composition was adjusted to pH 6.0 by addition of sodium hydroxide, and purified water was added until the weight of the composition was equal to 65 parts of the final weight. The composition was sterilised by filtration, flushing with sterile nitrogen. Then a clarified, steam sterilised concentrate of 2% xanthan gum was added to the solution of the drug and the obtained solution was homogenised by stirring. The solution was aseptically subdivided into sterile vials and sealed.

EXAMPLE 6

SOLUTION COMPOSITION

| | | |
|---|---|---|
| (S,S)-(-)-5,6-dihydro-4-ethylamino-6-methyl-4H-thieno[2,3-b]thiopyran-2-sulfonamide-7,7-dioxide monohydrochloride | | 2.226% |
| (S)-(-)-1-(tert-butylamino)-3-[(4-morpholino-1,2,5-thiadiazol-3-yl)oxy]-2-propanol maleate | | 0.684% |
| Xanthan Gum | | 0.5% |
| Sodium Chloride | | 0.15% |
| Sodium Hydroxide | QS | pH 5.6 |
| Benzalkonium Chloride | | 0.0075% |
| Purified Water | QS | 100% |

The active compounds, sodium chloride and benzalkonium chloride are dissolved in purified water. The pH of the composition is adjusted to pH 5.6 by addition of sodium hydroxide, and purified water is added until the weight of the composition was equal to 75 parts of the final weight. The composition is sterilised by filtration, flushing with sterile nitrogen. Then a clarified, steam sterilised concentrate of 2% xanthan gum is added to the solution of the drug and the obtained solution is homogenised by stirring. The solution is aseptically subdivided into sterile vials and sealed.

RESULTS

In attempts to improve the ocular bioavailability of dorzolamide in the albino rabbit, the effect of ophthalmic vehicles such as Gelrite™, Carbopol™, polyvinyl alcohol or cyclodextrin was investigated and all these approaches have produced only minor changes in bioavailability when compared with the TRUSOPT™ formulation. Bioadhesive solutions, suspensions of microparticles or ion-exchange resins have also been studied, however, we have found that whenever dorzolamide is bound to a carrier, the ocular bioavailability is reduced when compared with the TRUSOPT™ formulation.

Ocular bioavailability was improved by when hypotonic xanthan solutions of 1% and 1.5% dorzolamide were developed (hypotonicity: $\Delta t = -0.35°$ C.). When tested for ocular bioavailability in the albino rabbit, the 1.5% dorzolamidelxanthan gum hypotonic formulation was equivalent to 2% TRUSOPT™. A 2% dorzolamide/xanthan gum hypotonic solution at pH 5.6 was compared with 2% TRUSOPT™ in the albino and pigmented rabbits. The xanthan formulation generated an ocular bioavailability in the albino rabbit that was twice that of TRUSOPT™ 2%. The $C_{max}$ occurred at 1 hour in each ocular site and was approximately two fold higher with the hypotonic xanthan formulation.

The results obtained in the pigmented rabbits confirmed previous data with concentrations at 8 hours which were increased by 1.5 in the iris+ciliary body, with the hypotonic xanthan formulation.

Concentration of dorzolamide were measured by HPLC in various fluids and tissues of the pigmented rabbit eye at 1, 2, 4 and 8 hours after dosing with TRUSOPT™ (2% dorzolamide) or 2% dorzolamide in a hypotonic xanthan gum formulation. The instillation of the latter resulted in more dorzolamide in the eye especially at the early time points. For example, corneal, aqueous humor and iris-ciliary body values at 2 hours were 4.0-, 4.7-, 2.8-fold higher, respectively. Retinal, choroidal and scleral concentrations were also 1.7-, 3.5- and 2.2-fold higher at 2 hours. In contrast, values for dorzolamide in the red blood cell (9.69 vs. 9.51 µg/g) and plasma (0.20 vs. 0.25 µg/ml) were very similar after dosing with either TRUSOPT™ or the 2% dorzolamide/xanthan gum formulation. These findings indicate that the penetration of dorzolamide into the anterior and posterior portions of the eye is enhanced by the instillation of the drug in the hypotonic xanthan gum formulation and is independent of drug concentrations in the blood.

What is claimed is:

1. An ophthalmic composition for the treatment of ocular hypertension and glaucoma in a subject in need thereof, comprising a hypotonic solution of 0.1 to 2% (w/w) of xanthan gum and 0.5 to 5% (w/w) of a topical carbonic anhydrase inhibitor of the structural formula:

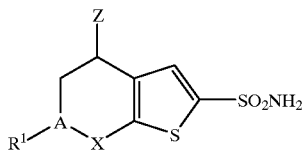

an individual diastereomer, an individual enantiomer or mixture thereof, or an ophthalmologically acceptable salt thereof, wherein:

A is carbon or nitrogen;
Z is —NHR or —OR;
R is $C_{1-6}$alkyl, either straight or branched chain;
$R^1$ is
  (a) hydrogen,
  (b) $C_{1-3}$alkyl, or
  (c) $C_{1-4}$alkoxy-$C_{1-4}$alkyl; and
X is —$SO_2$— or —C(O)—.

2. The composition of claim 1 wherein A is carbon, Z is —NHR, and X is —$SO_2$—.

3. The composition of claim 1 or 2 wherein:
R is
  a) —$CH_2CH_3$,
  b) —$CH_2CH_2CH_3$, or
  c) —$CH_2CH(CH_3)_2$; and
$R^1$ is
  a) hydrogen,
  b) —$CH_3$,
  c) —$CH_2CH_3$,
  d) —$CH_2CH_2CH_3$,
  e) —$CH_2CH_2CH_2OCH_3$, or
  f) —$CH_2OCH_2CH_3$.

4. The composition of any one of claims 1 to 3 wherein A is carbon; and wherein: R is —$CH_2CH_3$ and $R^1$ is —$CH_3$; or R is —$CH_2CH_2CH_3$ and $R^1$ is —$CH_2CH_2CH_2OCH_3$; or R is —$CH_2CH_3$ and $R^1$ is —$CH_2CH_2CH_3$; or R is —$CH_2CH(CH_3)_2$ and $R^1$ is hydrogen; or R is —$CH_2CH_3$ and $R^1$ is —$CH_2OCH_2CH_3$; and carbons 4 and 6 of the topical carbonic anhydrase inhibitor both have S absolute stereochemical configuration.

5. The composition of claim 1 wherein the topical carbonic anhydrase inhibitor is (S,S)-(-)-5,6-dihydro4-ethylamino-6-methyl-4H-thieno[2,3-b]thiopyran-2-sulfonamide-7,7-dioxide hydrochloride.

6. The composition of any one of claims 1 to 5 wherein the concentration of carbonic anhydrase inhibitor is 2.0% (w/w).

7. The composition of any one of claims 1 to 6 wherein the concentration of xanthan gum is 0.4 to 0.7% (w/w).

8. The composition of any one of claims 1 to 7 wherein the freezing point depression of the hypotonic solution is between –0.28° C. and –0.4° C.

9. The composition of any one of claims 1 to 7 wherein the hypotonicity of the solution is between 150 and 215 mOs/kg.

10. The composition of any one of claims 1 to 9 which additionally comprises about 0.01 to 1% (w/w) of a β-adrenergic receptor blocking agent, or an ophthalmologically acceptable salt thereof.

11. A composition of claim 10 wherein the concentratoion of β-adrenergic receptor blocking agent is about 0.1 to 0.5% (w/w).

12. A composition of claim 10 or claim 11 in which the β-adrenergic receptor blocking agent is timolol maleate.

13. A method of treating ocular hypertension or glaucoma which comprises the topical ocular administration to a patient in need of such treatment of a unit dose of the composition of any one of claims 1 to 12.

* * * * *